(12) United States Patent
Haerter et al.

(10) Patent No.: US 7,820,848 B2
(45) Date of Patent: Oct. 26, 2010

(54) PROCESS FOR THE PREPARATION OF STILBENE DERIVATIVES

(75) Inventors: Ralph Haerter, Biel-Benken (CH); Ulrike Lemke, Heidelberg (DE); Alexander Radspieler, Grenzach-Wyhlen (DE)

(73) Assignee: DSM IP Assets B.V., Te Heerlen (NL)

( * ) Notice: Subject to any disclaimer, the term of this patent is extended or adjusted under 35 U.S.C. 154(b) by 664 days.

(21) Appl. No.: 10/570,777

(22) PCT Filed: Aug. 31, 2004

(86) PCT No.: PCT/EP2004/009669

§ 371 (c)(1),
(2), (4) Date: Nov. 7, 2006

(87) PCT Pub. No.: WO2005/023740

PCT Pub. Date: Mar. 17, 2005

(65) Prior Publication Data

US 2007/0197819 A1    Aug. 23, 2007

(30) Foreign Application Priority Data

Sep. 5, 2003   (EP)   ................................. 03020123

(51) Int. Cl.
    C07C 69/00   (2006.01)
(52) U.S. Cl. .................................... 560/144
(58) Field of Classification Search ............ 560/144
    See application file for complete search history.

(56) References Cited

U.S. PATENT DOCUMENTS

| | | | |
|---|---|---|---|
| 2,748,160 A * | 5/1956 | Reynolds et al. ............ | 560/144 |
| 5,703,269 A | 12/1997 | Herrmann et al. | |
| 6,224,739 B1 | 5/2001 | Reetz et al. | |
| 6,392,111 B1 | 5/2002 | Reetz et al. | |
| 2002/0128478 A1 | 9/2002 | Krska et al. | |

FOREIGN PATENT DOCUMENTS

WO    WO 01/60774 A1    8/2001

OTHER PUBLICATIONS

Gessner Hawley, the Condensed Chemical Dictionary, 1971, Van Nostrand Reinhold Company, 8th ed., p. 455, three pages.*
Nebergall et al , College Chemistry wit hqualitative analysis, p. 89, 1980, pp. 3.*
Aldrich, Catalog Handbook of Fine Chemicals, 1998-1999, p. 601, 2 pages.*
Reynolds et al , J. Org. Chem. , 1953, 18(12), p. 1709-1715.*
Beletskaya and Cheprakov, "*The Heck Reaction As a Sharpening Stone of Palladium Catalysis*," Chem. Rev., 100, p. 3009 (2000).
Borne and Mauldin, "*Synthesis of C-3 Side-Chain Carboxylic Acid Cannabinoid Derivatives*," J. Heterocyclic Chem., 22, pp. 693-696 (1985).
Cristol et al., "*Photochemical Transformation., 48. The Nonconcertedness of Nucleofuge Loss and anti-Aryl Migration in Photochemical Wagner-Meerwein Rearrangements*," J. Am. Chem. Soc., 111, pp. 8207-8211 (1989).
Galbraith and Whalley, "*The Chemistry of Fungi. Part LIX. The Synthesis of (±)-Ascochitine*," J. Chem. Soc. (C)., pp. 3557-3559 (1971).
Guiso et al., "*A New Efficient Resveratrol Synthesis*," Tetrahedron Letters, 43, pp. 597-598 (2002).
Jaeger and Angelos, "*Stereochemistry of Photosolvolysis of a Chiral, $^{18}O$-Labeled I-Arylethyl Acetate*," Tetrahedron Letters, vol. 22, pp. 803-806 (1981).
Razzuk and Biehl, "*The Reaction of Various Methoxy-Substituted Haloarenes With Amines and Nitriles Under Aryne-Forming Conditions*," J. Org. Chem., 52, pp. 2619-2622 (1987).
Whitcombe et al., "*Advances in the Heck Chemistry of Aryl Bromides and Chlorides*," Tetrahedron Letters, 57, p. 7450 (2001).
Winn et al., "*Drugs Derived From Cannabinoids. 5. $\Delta^{6a,10a}$-Tetrahydrocannabinol and Heterocyclic Analogs Containing Aromatic Side Chains*," J. Med. Chem., vol. 19, No. 4, pp. 461-471 (1976).

* cited by examiner

Primary Examiner—Taylor Victor Oh
(74) Attorney, Agent, or Firm—Hoxie & Associates LLC

(57) ABSTRACT

A novel process for the preparation of resveratrol and piceatannol and esters thereof involving a Heck type reaction is disclosed. Also disclosed are novel intermediates in that process.

14 Claims, No Drawings

PROCESS FOR THE PREPARATION OF STILBENE DERIVATIVES

The present invention is concerned with a novel process for the preparation of styryl derivatives. More particularly, the present invention is concerned with a novel process for the preparation of resveratrol and piceatannol, and esters thereof.

Resveratrol as occurring in nature, by systematic name: 3,4',5-trihydroxystilbene, is a known compound which has gained interest because of its biological properties, see, e.g., International patent application WO 01/60774. Piceatannol, also a known compound, is 3,3',4,5'-tetrahydroxystilbene.

Processes for the preparation of resveratrol have been disclosed, inter alia, in WO 01/60774 and Tetrahedron Letters 43 (2002) 597-598. The latter reference describes a process wherein resveratrol is prepared by a multistep reaction sequence starting with 3,5-dihydroxybenzaldehyde and involving a Heck reaction of 3,5-dihydroxystyrene with 4-acetoxy-iodobenzene in a yield of 70%. The process of the present invention utilizes a more readily available starting material and proceeds in less steps and superior yield, thus providing a technically more attractive approach to resveratrol and piceatannol and derivatives, such as esters, thereof.

In one aspect, the present invention is concerned with a process for the preparation of resveratrol and piceatannol and esters thereof which comprises reacting a compound of the formula I

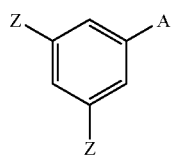
(I)

with the compound of the formula II

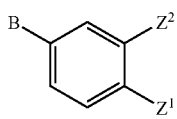
(II)

wherein Z and $Z^1$ are, independently, protected hydroxy groups; $Z^2$ is hydrogen or $Z^1$; and one of A and B is vinyl and the other is chloro or bromo;

to obtain a compound of the formula III

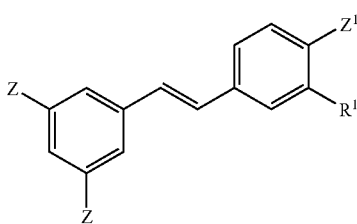
(III)

wherein Z and $Z^1$ are as above, and $R^1$ is hydrogen or $Z^1$;

cleaving the hydroxy protecting groups from the compound of the formula III to obtain resveratrol or piceatannol, if desired, converting the so-obtained resveratrol or piceatannol into an ester and, if further desired, isomerizing (E)-resveratrol or ester thereof or (E)-piceatannol or ester thereof to obtain the corresponding (Z)-isomer.

The terms "resveratrol" and "piceatannol" as used herein denote the (E) as well as the (Z) isomer and mixtures thereof. In a preferred aspect, the present invention is concerned with the preparation of the (E) isomers. More preferably, the present invention is concerned with the preparation of (E)-resveratrol.

The protecting groups in the hydroxy groups Z and $Z^1$ may be any cleavable protecting groups. Examples of such protecting groups are electron-withdrawing groups, e.g., acyl groups such as straight or branched alkanoyl groups, especially acetyl, or aroyl groups, e.g., benzoyl; carbonate groups such as methoxycarbonyl, ethoxycarbonyl and benzyloxycarbonyl; as well as carbamate groups, e.g., methylcarbamoyl; and sulfonates, e.g., toluenesulfonate or methansulfonate. Further examples of protecting groups Z and $Z^1$ are non electron-withdrawing groups such as acetal groups e.g., methoxymethylene, ethoxyethylene, methoxymethyl, benzyloxymethyl, tetrahydropyranyl, 1-ethoxyethyl and 1-methoxy-1-methylethyl, or silyl ethers such as trimethylsilyl, triisopropylsilyl and t-butyldimethylsilyl. The introduction and cleavage of such protecting groups is well known in the art, see, e.g. T. W. Greene and P. G. M. Wuts (eds.) Protective groups in organic synthesis. $3^{rd}$ edition, John Wiley 1999. 246-287 and citations therein.

The reaction of a compound of the formula I with a compound of the formula II can be carried out under conditions known per se for a Heck reaction. Suitably, about equimolar amounts of the compounds of formulas I and II are used. As a solvent for the reaction, any inert organic solvent can be used, examples of such solvents being organic solvents, e.g. hydrocarbons such as toluene, ethers such as dioxan, nitriles such as acetonitrile, ketones such as acetone, and amides such as dimethylformamide or N-methylpyrrolidone. Further, the reaction is suitably carried out in the presence of a base which may be an inorganic base, e.g., a carbonate or hydrogencarbonate such as sodium carbonate or hydrogen-carbonate, tert. phosphates such as $K_3PO_4$, or an organic base, e.g., an amine such as triethyl amine or diisopropyl ethylamine; or an alkali acetate such as sodium acetate. The base is used in an at least equimolar amount, based on the reactant I and II, respectively. Further, according to general conditions for a Heck reaction, a catalyst comprising a Pd source, such as palladium acetate or $Pd(dba)_2$ and a stabilizing ligand e.g. a phosphine such as tri-o-tolylphosphine, or an ammonium salt, such as tetrabutylammonium chloride, are added. Moreover, palladium catalysts and palladacycles e.g. oxime-derived palladadium complexes or trans-di(µ-acetato)-bis[o-tolylphosphino)benzyl]palladiumII (see e.g. Advanced synthesis and catalysis 344 (2002), 172-183 and Journal of Organometallic chemistry 576 (1999), 23-41) proved to be convenient Pd sources.

The reaction is suitably carried out at normal or elevated pressure and at elevated temperature, e.g. at a temperature up to the boiling point at the appropriate pressure of the solvent used and in an inert atmosphere, e.g. under argon.

The so-obtained compound of the formula III can be converted into resveratrol or an ester thereof by cleaving the protecting group and, if desired, esterification of the hydroxy groups. The cleavage of the protected hydroxy groups Z and $Z^1$ can be accomplished by methods known per se, as cited above. Cleavage of a protected hydroxy group, e.g., an acetoxy group, can be achieved e.g. by basic hydrolysis such as treatment with alcoholic alkali hydroxide at elevated temperature. In a preferred aspect of the invention, the protected hydroxy groups are acetoxy groups and are hydrolyzed under substantially neutral conditions. Such hydrolysis of a compound of formula III wherein Z and $Z^1$ or Z, $Z^1$ and $R^1$ are acetoxy, can be effected by treatment with ammonium acetate, e.g., by adding an aqueous solution (up to 60%) of ammonium acetate to a solution of the compound of formula III in an appropriate solvent, e.g. methanol or ethanol at about room temperature or elevated temperature up to the boiling point, see also Tetrahedron 59 (2003) 1049-1054. After cleavage of the protecting groups, resveratrol and piceatannol, respectively, can be isolated from the reaction mixture by acidification (after basic hydrolysis) and extraction with an organic solvent, e.g. ethyl acetate. If desired, resveratrol and piceatannol can be converted into an ester by esterification with the appropriate acid or a reactive derivative thereof by methods known per se or can be submitted to isomerisation.

Esters of resveratrol and piceatannol, respectively, may be derived from unsubstituted or substituted, straight or branched chain alkyl groups having 1 to 26 carbon atoms or from unsubstituted or substituted, straight or branched chain aliphatic, araliphatic or aromatic carboxylic acids having 1 to 26 carbon atoms.

While by the process of the invention (E)-resveratrol or (E)-piceatannol is obtained as the sole or substantially the sole reaction product, the (E)-isomer can, if desired, be isomerized to the (Z)-isomer by known methods, see, e.g., Agric. Food Chem. 43; 1995; 1820-1823.

In another aspect of the invention, the compound of formula I as used in the above reaction is prepared from a compound of the formula IV

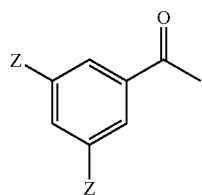

(IV)

wherein Z is as above.

More particularly, in accordance with that aspect of the invention, a compound of formula I is prepared by reducing a compound of formula IV to obtain a compound of the formula V

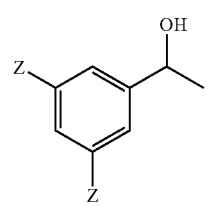

(V)

wherein Z is as above, and dehydrating the compound of the formula V.

A compound of formula IV can be reduced to form a compound of formula V by catalytic hydrogenation, e.g. using a noble metal catalyst, such as Pd or Pt on charcoal, or an activated Ni catalyst such as Raney Ni, in alcoholic, e.g. methanolic solution. The reaction conditions for the hydrogenation are not narrowly critical and the hydrogenation may be carried out at atmospheric pressure or elevated pressure. Suitably, hydrogenation using $H_2$ in the presence of a noble metal catalyst is carried out at elevated hydrogen pressure, e.g., up to 200 bar, particularly at about 10 bar to about 30 bar $H_2$, and at a temperature of about 20° C. to about 50° C. The compounds of formula V are novel compounds and as such are also an object of the present invention. They can be isolated by conventional procedures such as chromatography of the reaction solution on silica gel. The compounds of formula IV are known or can be prepared from the known dihydroxyacetophenone by protecting the hydroxy groups in a manner known per se, see above. The compounds of formula V can be converted into compounds of formula I by procedures know per se for the conversion of alcohols to olefins. Suitably, the hydroxy group in a compound of formula V is first converted into a leaving group to yield a compound of the formula VI

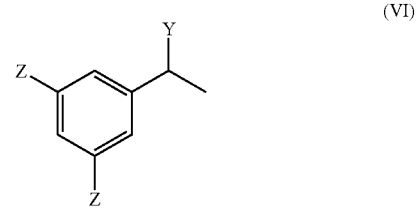

(VI)

wherein Y is a leaving group, and Z is as above, followed by elimination of the leaving group. Examples of leaving groups in this reaction step are halogens, e.g. chlorine or bromine; or ester groups, especially sulfonyloxy groups such as p-tosyloxy or mesyloxy, or carboxylic acid ester groups such as acetoxy; or carbonates, or xanthate esters. The introduction and elimination of the leaving group can be carried out using conventional methods. Thus, the compound of formula V can be reacted with a halogenating agent, e.g., with phosphorous tribromide, to yield a compound of formula VI wherein Y is bromo. Treatment of a compound of formula VI with a dehydrohalogenating agent such as $LiBr/Li_2CO_3$ produces a compound of formula I. Dehydration of a compound of formula V to yield a compound of formula I may also be achieved by esterifying the hydroxy group with a reactive sulfonic acid derivative such as a mesyl or tosyl halogenide or anhydride to yield a compound of formula VI wherein Y is the sulfonyloxy portion of the sulfonic acid derivative used to esterify the hydroxy group in compound IV. Further, a compound of formula V can be reacted with an alkyl chloroformate, e.g. ethyl chloroformate to yield a compound of formula VI wherein Y is alkyl-O—CO—O—.

The conversion of a compound of formula VI wherein Y is an ester group to a compound of formula I is suitably carried out in an appropriate inert, acid-stable organic solvent, which may be an apolar solvent e.g., a hydrocarbon such as toluene, or a halogenated hydrocarbon such as methylene chloride, or a polar solvent, such as an ester, e.g., ethyl acetate; or an amide, e.g. DMF or NMP or dimethylsulfoxide, at temperatures up to the boiling point of the solvent used. Said conversion may also be carried out in gas phase, e.g., at temperatures up to 800° C., if desired, also in a continuous mode. The pyrolytic elimination of a leaving group Y from the compound VI is especially suited in case of Y representing alkyl-OCOO—. It will be appreciated that suitable conditions for the cleavage of a particular leaving group can be readily determined by those skilled in the art.

The compounds of formula VIII are novel compounds and as such are also an object of the present invention.

Further, the conversion of a compound of formula V to a compound of formula I may be accomplished also directly by treatment of the compound of formula V with inorganic acids, such as sulfuric acid or hydrogensulfates, or phosphoric acid; or organic acids such a formic acid, or p-toluene sulfonic acid; or acidic ion exchange resins which may be used in catalytic amounts or in amounts up to equimolar amounts.

The following examples illustrate the invention further.

EXAMPLE 1

A 500 ml autoclave was charged with 20 g (85 mmol) of 3,5-diacetoxyacetophenone, 2 g of palladium on charcoal (catalyst E101 CA/W 5%, Degussa, Germany) and 350 ml of methanol. The autoclave was flushed three times with hydrogen (3 bar), the mixture was stirred and hydrogenation was carried out at 30 bar hydrogen pressure for two hours. After flushing the solution twice with 3 bar nitrogen the catalyst was removed by filtration over Hyflo Super Cel®. Evaporation of the solvent left 19.2 g of a slightly brown oil, which was further purified by flash-chromatography on silica gel using n-hexane/ethyl acetate (5:2) as eluent mixture giving 18.4 g of 1-(1-hydroxyethyl)-3,5-diacetoxybenzene as a colorless oil (81 mmol, GC 98%).

EXAMPLE 2

10 g (42 mmol) of 1-(1-hydroxyethyl)-3,5-diacetoxybenzene in 80 ml of DMF were placed into a 250 ml 2-necked flask equipped with a magnetic stirrer. The flask was flushed thoroughly with argon and the mixture was cooled down to 0° C. A solution of 4.06 ml (42 mmol) of phosphorous tribromide in 30 ml $CH_2Cl_2$ was slowly added and the reaction was allowed to complete within three hours at 0° C. $CH_2Cl_2$ was evaporated and elimination of hydrogen bromide from the intermediate 1-(1-bromoethyl)-3,5-diacetoxybenzene was achieved using 21.38 g (0.24 mol) lithium bromide and 20.74 g lithium carbonate (0.28 mol). The mixture was stirred at 120° C. for 18 hours under a slight argon stream, then poured into 156 ml of ethyl acetate and extracted in two portions against 300 ml ice water. The organic layer washed with brine and saturated $NH_4Cl$ solution and dried over $MgSO_4$ giving 5.18 g (56%) of the desired product, 3,5-diacetoxystyrene, and 3.14 g (42%) of monoacetoxystyrene.

The product mixture was solved in 10 ml of pyridine and treated with 2.33 ml (21.2 mmol) of acetic anhydride without further purification for 15 h at room temperature. The resulting solution was poured into 100 ml ethyl acetate and extracted three times against 100 ml of 1N HCl. The organic layer washed twice with 50 ml of brine and dried over $MgSO_4$. After evaporation of the solvent chromatographic purification over silica gel using a 7:2 (v/v) mixture of n-hexane and ethyl acetate gave 8.04 g of 3,5-diacetoxystyrene as a colorless oil (36.5 mmol, 87%).

EXAMPLE 3 a) 0.5 g (2.1 mmol) of 1-(1-hydroxyethyl)-3,5-diacetoxybenzene were placed into a 25 ml flask and dissolved in 0.31 ml (3.78 mmol, 1.8 eq) pyridine. 2.52 mmol (1.2 eq) acetic anhydride were added dropwise while stirring the reaction mixture. The conversion was carried out at 60° C. for three hours. The mixture was diluted with 5 ml of ethyl acetate and extracted once against 5 ml 1N HCl. The organic layer washed twice with saturated ammonium chloride solution and dried over magnesium sulfate. After evaporation of the solvent 419 mg (1.49 mmol, 71%) of 1-(1-acetoxyethyl)-3,5-diacetoxybenzene were obtained with a purity of 99% (determined by GC).

b) 20 g of 1-(1-acetoxyethyl)-3,5-diacetoxy-benzene (71 mmol) were dissolved in 20 ml toluene and placed into a feed vessel connected to a pyrolytic tube filled with Raschig rings. The tube was heated to 500° C. and the neat mixture was immediately added. Conversion of the alcohol was achieved within two minutes. The column was rinsed with toluene. Work-up was conducted by extracting the crude material in toluene twice with 200 ml water. The aqueous solutions were reextracted with toluene, the organic layers were combined, dried over magnesium sulfate and the solvent removed under reduced pressure giving 6.6 g 3,5-diacetoxystyrene (42%).

EXAMPLE 4

(a) In a 100 ml flat bottom flask 12.7 g (53 mmol) of 1-(1-hydroxy)-ethyl-3,5-diacetoxybenzene are dissolved in 38 ml toluene and 5.6 g (71 mmol) pyridine. Under argon 6.7 g (62 mmol) ethyl chloroformate are added slowly at a temperature below 50 Co. The mixture is additionally stirred for 30 minutes. After cooling to room temperature 13 ml water are added into the reaction mixture and intensively mixed. After phase separation the organic layer is washed with 13 ml of 1N HCl. The organic layer is washed with water until neutral and the solvent is evaporated in vacuum giving 16.27 g acetic acid 3-acetoxy-5-(1-ethoxycarbonyloxy-ethyl)-phenyl ester (99%).

(b) 20.0 g acetic acid 3-acetoxy-5-(1-ethoxycarbonyloxy-ethyl)-phenyl ester is dissolved in 92.5 ml toluene and the mixture is continuously conducted through a glass tube filled with ceramic packing at 475° C. After cooling the reaction mixture to room temperature the solvent is evaporated in vacuum and 12.8 g (90%) pure 3,5-diacetoxystyrene is isolated.

EXAMPLE 5

A 3-necked flask equipped with condenser and magnetic stirrer and connected to an argon pipeline was placed into an oil bath and charged with 1 g (4.5 mmol) of 3,5-diacetoxystyrene, 0.98 g (4.54 mmol) of 4-acetoxybromobenzene and 0.58 g (5.5 mmol) of sodium bicarbonate in 20 ml of DMF. The mixture was de-aerated by alternately purging with argon and evacuating the flask. Into the reaction vessel were added 62.8 mg (0.2 mmol) of tri-o-tolylphosphine and 15.3 mg (0.07 mmol) of palladium acetate in de-aerated DMF. The resulting solution was heated to 100° C. and refluxed for 18 hours under argon. Purification was carried out by pouring the reaction mixture into 50 ml of ice-cold water and extracting with ethyl acetate. The aqueous layer was saturated with sodium chloride and reextracted with 20 ml of ethyl acetate. The organic layers were combined, washed with 50 ml of saturated $NH_4Cl$ solution and 50 ml of brine, dried over $MgSO_4$, and the solvent evaporated in a vacuum, giving 1.76 g of a yellow solid. The raw product was acetylated using 0.8 ml of pyridine (10 mmol) and 1.1 g of acetanhydride (10 mmol) in 20 ml of ethyl acetate. The mixture was refluxed for one hour at 80° C. After cooling at room temperature, the crude material was diluted with 30 ml of ethyl acetate and extracted four times against 1N HCl. The organic layer was dried over $MgSO_4$ and the solvent removed. Chromatographic purification over silica gel, employing a 5:2 (v/v) mixture of n-hexane and ethyl acetate as eluting agent, gave 1.2 g of (E)-3,4',5-triacetoxystibene (3.4 mmol, 75%).

EXAMPLE 6

A flask equipped with magnetic stirrer was charged with 50 mg (0.23 mmol, 1 eq) of 3,5-diacetoxystyrene, 49 mg (0.23 mmol) of 4-acetoxybromobenzene, 46 mg (0.27 mmol) of NaHCO$_3$ and 78 mg (0.54 mmol, 2.4 eq) of tetrabutylammoniumchloride. The reactants were suspended in 2 ml DMF and the mixture was flushed with argon and then evacuated. The argon flushing and evacuation procedure was carried out three times. The reaction was started by adding 0.76 mg of palladium acetate in 50 µl of de-aerated DMF (3 µmol, 1.5 mol %), and stirred at 100° C. for three hours. Work-up of the reaction mixture following the procedure of Example 5 gave (E)-3,4',5-triacetoxystilbene.

EXAMPLE 7

A 10 ml Schlenk tube equipped with magnetic stirrer was charged with 119 mg (0.7 mmol) of 4-acetoxychlorobenzene, 200 mg (0.84 mmol, 1.2 eq) of 3,5-diacetoxystyrene, 177 mg (0.84 mmol, 1.2 eq) of potassium triphosphate, 5 mg of diadamantyl-n-butylphosphine (0.014 mmol, 2 mol %) and 3.7 mg (0.003 mmol, 0.5 mol %) of tris(dibenzylideneacetone)-dipalladium chloroform complex. The tube was evacuated and flushed with argon three times, and 2 ml of de-aerated DMAc was added under inert conditions. The reaction was carried out under stirring for 15.5 hours at 120° C. Work-up of the reaction mixture following the procedure of Example 5 gave (E)-3,4',5-triacetoxystilbene.

EXAMPLE 8

A 10 ml Schlenk tube equipped with magnetic stirrer was charged with 59 mg (0.7 mmol) of 4-acetoxychlorobenzene, 100 mg (0.84 mmol, 1.2 eq) of 3,5-diacetoxystyrene, 125 mg of cesium carbonate (0.38 mmol, 1.1 eq), 5 µl of P(t-Bu)$_3$ (0.02 mmol, 6 mol %) and 5.57 mg (0.01 mmol, 1.5 mol %) of tris(dibenzylideneacetone)-dipalladium chloroform complex. The tube was evacuated and flushed with argon three times and 1 ml de-aerated dioxane was added under inert conditions. The reaction was carried out under stirring for 19 hours at 120° C. Work-up was conducted following the procedure of Example 5 and gave (E)-3,4',5-triacetoxystilbene.

EXAMPLE 9

A 100 ml flat-bottomed flask was charged with 10.8 g 4-acetoxybromobenzene (50 mmol), 11.7 g 3,5-diacetoxystyrene (50 mmol) and 8.3 g potassium carbonate (60 mmol, 1.2 eq). The components were dissolved in 35 ml NMP and the flask was purged with argon. Heck reaction was started by adding 6.9 mg (0.05 mol %) of an acetophenon-oxim derived palladium catalyst (CAS No. 32679-19-9, see also palladacycle 16a as disclosed in Adv. Synth. Catal. 2002, 344, No2., p. 173) dissolved in 5 ml NMP under inert conditions. The reaction mixture was stirred for three hours at 150° C. and subsequently cooled to room temperature. 50 ml ethyl acetate was added to the crude material and the obtained solution extracted 4 times against 50 ml 1N HCl. The aqueous solution was reextracted twice with 50 ml ethyl acetate, the organic layers were combined, dried over MgSO$_4$ and the solvent was removed. Subsequent work-up was conducted following the procedure in Example 5. The isolated yield of 3,4',5-triacetoxystilbene was 17.7 g (94%)

EXAMPLE 10

50 mg (0.14 mmol) of (E)-3,4',5-triacetoxystilbene was dissolved in 3 ml methanol and degassed with argon. 8 mg (0.14 mmol) of potassium hydroxide in 0.5 ml methanol were added dropwise under a slight argon stream and the mixture was heated for 30 minutes to 65° C. The obtained solution was neutralized with 1 N hydrochloric acid, poured into 10 ml of ethyl acetate and extracted 3× against 5 ml of brine. The organic phase was dried over MgSO$_4$ and the solvent removed in vacuo giving 30 mg of resveratrol (0.13 mmol, 92%).

EXAMPLE 11

40 g (0.168 mol) of 3,5-diacetoxy-1-(1-hydroxy)-ethylbenzene were placed into a 250 ml flat bottom flask and under argon 19.6 ml (0.2 mol, 1.2 eq) acetanhydride and 18.9 ml (0.2 mol, 1.2 eq) pyridine were slowly added. The neat mixture was heated to 80° C. for one hour. After cooling to room temperature 200 ml ethyl acetate were poured into the raw material and the mixture was extracted 4 times against 100 ml of 1N HCl. The organic layer was dried over magnesium sulfate and the solvent evaporated in vacuo giving 42.4 g of 3,5-diacetoxy-1-(1-acetoxy)-ethylbenzene (97%).

EXAMPLE 12

6.32 g 3,5-diacetoxy-1-(1-hydroxy)-ethylbenzene (23 mmol) and 12.3 ml triethylamine (87.73 mmol, 3.81 eq) were dissolved in 50 ml toluene and cooled to 0° C. 6.26 ml of methane sulfonylchloride (79.76 mmol, 3.46 eq) were diluted in 5 ml toluene and the reagent was added dropwise to the solution of the alcohol. The mixture was stirred for 2.5 hours at 0° C. The work-up was conducted pouring 40 ml of saturated ammonium chloride solution to the raw reaction solution. The organic layer was separated and extracted once against 40 ml saturated ammonium chloride solution and once against 30 ml sodium hydrogen carbonate and dried over magnesium sulfate. The solvent evaporated in vacuo to give 8.27 g of 3,5-diacetoxy-1-(1-methylsulfonyl)-ethylbenzene with a purity of 80.7% (GC).

EXAMPLE 13

5 g 3,5-diacetoxy-1-(1-methylsulfonyl)-ethylbenzene are (13.06 mmol) were dissolved in 20 ml toluene and 1.75 ml of diisopropyamine (12.41 mmol, 0.95 eq) were added slowly at room temperature under stirring. The mixture was heated to 180° C. for 3.5 hours and after cooling to room temperature the solution was extracted twice against 60 ml saturated ammonium chloride solution. Afterwards, the organic layer washed with 50 ml water and dried over magnesium sulfate. Evaporation of the solvent under reduced pressure gave 2.9 g of 3,5-diacetoxystyrene (86%) with a purity of 85% (determined by GC).

EXAMPLE 14

0.57 g (3 mmol) of 3,4-dihydroxy-bromobenzene (synthesized according to Journal of Material Chemistry 10(7), 2000, 1519-1526, from commercially available 3,4-dimethoyxbromobenzene. 0.57 g (3 mmol) were dissolved in 0.31 ml (3.78 mmol) pyridine. 6.6 mmol acetic anhydride were added dropwise to the reaction mixture while stirring. The reaction was carried out at 60° C. for three hours. The mixture was diluted with 5 ml of ethyl acetate and extracted once against 5 ml 1N HCl. The organic layer washed twice with saturated ammonium chloride solution and dried over magnesium sulfate. After evaporation of the solvent 0.79 g (2.9 mmol, 97%) 3,4-diacetoxybromobenzene were obtained with a purity of 99%.

EXAMPLE 15

A 10 ml Schlenk tube equipped with magnetic stirrer is charged with 218 mg (0.8 mmol) 3,4-diacetoxybromobenzene, 176 mg (0.84 mmol) 3,5-diacetoxystyrene, 187 mg potassium carbonate (0.9 mmol) and 0.22 mg (0.1 mol %) of the acetophenon-oxim derived palladium catalyst CAS No. 32679-19-9 as used in Example 9. The tube was evacuated and flushed with argon three times and 1 ml de-aerated DMF was added under inert conditions. The reaction was carried out with stirring for 19 hours at 150° C. Work-up was conducted following the procedure of Example 5 and to give (E)-3,3', 4',5-tetraacetoxystilbene.

EXAMPLE 16

2.6 g (17.5 mmol) 2-mercaptopyridine-1-oxid was dissolved in 30.0 ml bromotrichloromethane and heated to reflux. A mixture of 4.04 g (15 mmol) 3,5-diacetoxybenzoyl-chloride and 433 mg (2.5 mmol) 2,2'-azobisisobutyronitril dissolved in 30.0 ml bromotrichlioromethane were added dropwise at the same temperature. After additional 2 hours of refluxing the reaction mixture was cooled to room temperature and concentrated in vacuum. Chromatographic purification over silica gel employing a 9:1 (v/v) mixture of n-hexane and ethyl acetate as eluting agent yielded 2.4 g of 3,5-diacetoxybromobenzene (8.7 mmol, 58%).

EXAMPLE 17

A 10 ml Schlenk tube equipped with a magnetic stirrer is charged with 218 mg (0.8 mmol) 3,5-diacetoxybromobenzene, 136 mg (0.84 mmol) 4-acetoxystyrene, 187 mg potassium carbonate (0.9 mmol) and 0.22 mg (0.1 mol %) of the acetophenon-oxim derived palladium catalyst CAS No. 32679-19-9 as used in Example 9. The tube was evacuated and flushed with argon three times and 1 ml de-aerated DMF was added under inert conditions. The reaction was carried out under stirring for 15 hours at 150° C. Work-up was conducted following the procedure of Example 4 and to give (E)-3,4',5-triacetoxystilbene.

EXAMPLE 18

2.10 g (6.0 mmol) triacetoxystilbene were dissolved under reflux in 19.3 ml methanol and 39 ml ammonium acetate solution (25%) was added to the solution. The reaction mixture was stirred for three hours at the same temperature and afterwards the methanol was distilled off. By cooling to 5° C. the product crystallized and could be filtered off. 1.33 g (5.82 mmol, 97%) resveratrol were obtained as a pure compound. The mother liquor was purified by extraction with methyl-butyl-ether and neutralized with ammonia. After concentration under reduced pressure the solution was used again for the described reaction.

What is claimed is:

1. A process for the preparation of resveratrol or piceatannol, or an ester of either, which process comprises reacting, in about equimolar amounts and under Heck reaction conditions, a compound of formula I

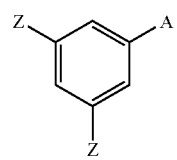

with a compound of formula II

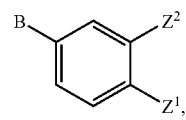

wherein Z and $Z^1$ is each, independently, a protected hydroxy group; $Z^2$ is hydrogen or a protected hydroxy group; and one of A and B is vinyl and the other is chloro or bromo;

to obtain a compound of formula III

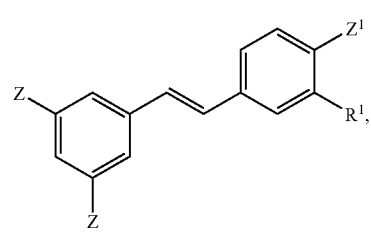

wherein Z and $Z^1$ are as defined above, and $R^1$ is hydrogen or a protected hydroxy group;

then cleaving the hydroxy protecting groups from the compound of formula III under basic or substantially neutral hydrolysis to obtain resveratrol or piceatannol, and, optionally, converting the so-obtained resveratrol or piceatannol into an ester thereof, and, optionally, isomerizing (E)-resveratrol or ester thereof or (E)-piceatannol or ester thereof to obtain the corresponding (Z)-isomer.

2. The process according to claim 1, wherein $R^1$ and $Z^2$ are each hydrogen, to obtain resveratrol.

3. The process according to claim 1, wherein A is vinyl and B is chloro or bromo.

4. The process according to claim 1, wherein each protected hydroxy group, independently, is an acetoxy group.

5. The process according to claim 4, wherein the acetoxy groups in the compound of formula III are hydrolyzed under substantially neutral conditions.

6. The process according to claim 5, wherein the hydrolysis is carried out using ammonium acetate.

7. The process according to claim 1, wherein a compound of formula I, wherein A is vinyl, is prepared from a compound of formula IV

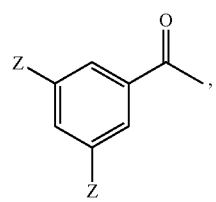

wherein each Z, independently, is a protected hydroxy group, by reducing the carbonyl group of a compound of formula IV by catalytic hydrogenation with a noble metal catalyst or an activated Ni catalyst at an elevated hydrogen pressure of up to 200 bar and a temperature of about 20-to-about 50° C. to obtain the compound of formula V,

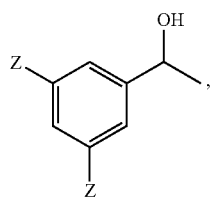
(V)

wherein Z is as defined above, and dehydrating the compound of formula V, or by converting the hydroxy group of a compound of formula V into a leaving group to yield a compound of formula VI,

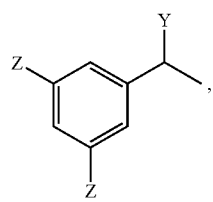
(VI)

wherein Y is bromine, sulfonyloxy, a carboxylic acid ester group, a carbonate ester group or a xanthate ester group, and eliminating HY from the compound of formula VI to yield a compound of formula I.

8. The compound of formula V

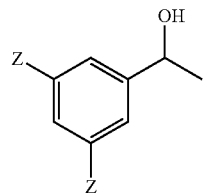
(V)

which is 1-(1-hydroxyethyl)-3,5-diacetoxybenzene.

9. A compound of formula VI

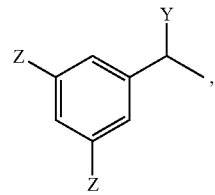
(VI)

wherein Y is bromine, sulfonyloxy, a carboxylic acid ester group, a carbonate ester group or a xanthate ester group, and each Z, independently, is a protected hydroxy group.

10. The compound according to claim 9, which is 1-(1-bromoethyl)-3,5-diacetoxybenzene.

11. The compound according to claim 9, which is 1-(1-acetoxyethyl)-3,5-diacetoxybenzene.

12. The process according to claim 2, wherein A is vinyl and B is chloro or bromo.

13. The process according to claim 2, wherein each protected hydroxy group, independently, is an acetoxy group.

14. The process according to claim 12, wherein each protected hydroxy group, independently, is an acetoxy group.

* * * * *